United States Patent [19]

McKinnie et al.

[11] Patent Number: 5,017,728
[45] Date of Patent: May 21, 1991

[54] TETRABROMOBISPHENOL-A PROCESS

[75] Inventors: Bonnie G. McKinnie; Daniel A. Wood, both of Magnolia, Ark.

[73] Assignee: Ethyl Corporation, Richmond, Va.

[21] Appl. No.: 569,850

[22] Filed: Aug. 20, 1990

[51] Int. Cl.$^5$ .................... C07C 37/62; C07C 39/367
[52] U.S. Cl. .................... 568/726; 422/224; 422/225; 568/723; 568/724; 568/776; 568/779
[58] Field of Search ............... 568/726, 776, 779, 723, 568/724, 774; 422/224, 225

[56] References Cited

U.S. PATENT DOCUMENTS

| | | | |
|---|---|---|---|
| 3,182,088 | 5/1965 | Hennis | 260/619 |
| 3,644,096 | 2/1972 | Lewis et al. | 23/263 |
| 3,818,938 | 6/1974 | Carson | 137/604 |
| 3,868,423 | 2/1975 | Montanari et al. | 260/619 A |
| 4,112,242 | 9/1978 | Swietoslawski et al. | 568/726 |
| 4,451,675 | 5/1984 | Bounds | 568/726 |
| 4,548,788 | 10/1985 | Morris et al. | 422/109 |
| 4,628,124 | 12/1986 | McKinnie et al. | 568/726 |
| 4,701,568 | 10/1987 | McKinnie et al. | 568/726 |
| 4,783,556 | 11/1988 | Mitchell et al. | 568/726 |

FOREIGN PATENT DOCUMENTS

| | | | |
|---|---|---|---|
| 2005259 | 2/1970 | Fed. Rep. of Germany | 568/779 |
| 96774 | 7/1960 | Norway | 422/225 |
| 949306 | 2/1964 | United Kingdom . | |

OTHER PUBLICATIONS

Chemical Abstract No. 174372c.
Chemical Abstract No. 173951d.
Chemical Abstract No. 110003e.
Chemical Abstract No. 186315h.

Primary Examiner—Werren B. Lone
Attorney, Agent, or Firm—David E. LaRose

[57] ABSTRACT

Tetrabromobisphenol-A is made in high purity and increased yield by adding a methanol-bromine solution to a methanol bisphenol-A solution with vigorous agitation. The amount of methanol in the reaction vessel is adjusted to yield a ratio of tetrabromobisphenol-A to methanol when the reaction is substantially complete that provides a lower amount of Hbr impurity in the tetrabromobisphenol-A product. An increased recovery of tetrabromobisphenol-A product is achieved by adjusting the water added to the reaction vessel when the bromination reaction is essentially complete.

16 Claims, 1 Drawing Sheet

TETRABROMOBISPHENOL-A PROCESS

BACKGROUND OF THE INVENTION

This invention relates to a process for preparing a tetrabromobisphenol-A predominant product which has a low organic and HBr impurity content.

4,4'-isopropylidenebis(2,6-dibromophenol) is a well known commercial flame retardant and is usually referred to a tetrabromobisphenol-A (hereinafter "TBBPA"). The literature is replete with processes for the manufacture of TBBPA, see, for example, U.S. Pat. Nos. 3,234,289, 3,363,007, 3,546,302, 3,868,423, 3,929,907, 4,013,728, 4,036,894 and U.S. Pat. No. 4,701,568. Two process which produce TBBPA predominant products having particularly low organic impurity contents are described in U.S. Pat. No. 4,628,124 and U.S. Pat. No. 4,783,556.

In the '124 process, a methanol-bromine solution is added to a methanol-bisphenol-A solution with vigorous agitation. In this process the methanol-bromine solution is conveniently added in a dip-tube beneath the surface of the methanol-bisphenol-A solution. The process in U.S. Pat. No. 4,783,556 is similar except that a product having a lower organic impurity content is obtained by impinging a methanol-bromine stream and a bisphenol-A and methanol containing stream in an impingement mixer and then conducting the resultant mixture to a reaction vessel. It has been found that this procedure, while yielding a very pure product as far as organic impurities is concerned, is not superior to the '124 process in regard to the HBr content of the TBBPA predominant product.

SUMMARY OF THE INVENTION

It has now been discovered that the amount of hydrobromic acid (HBr) impurity in a tetrabromobisphenol-A (TBBPA) predominant product can be significantly reduced while maintaining a low level of organic impurity. This improved TBBPA predominant product can be achieved by having a certain ratio of a methanol solvent to the TBBPA predominant product when the bromination is substantially complete. Another feature of the process of this invention is an increase in the recovery of the desired TBBPA product thus allowing the use of a smaller sized batch. Other features of the process of this invention will be evident from the ensuing description.

DESCRIPTION OF THE PREFERRED EMBODIMENTS

Figure 1:
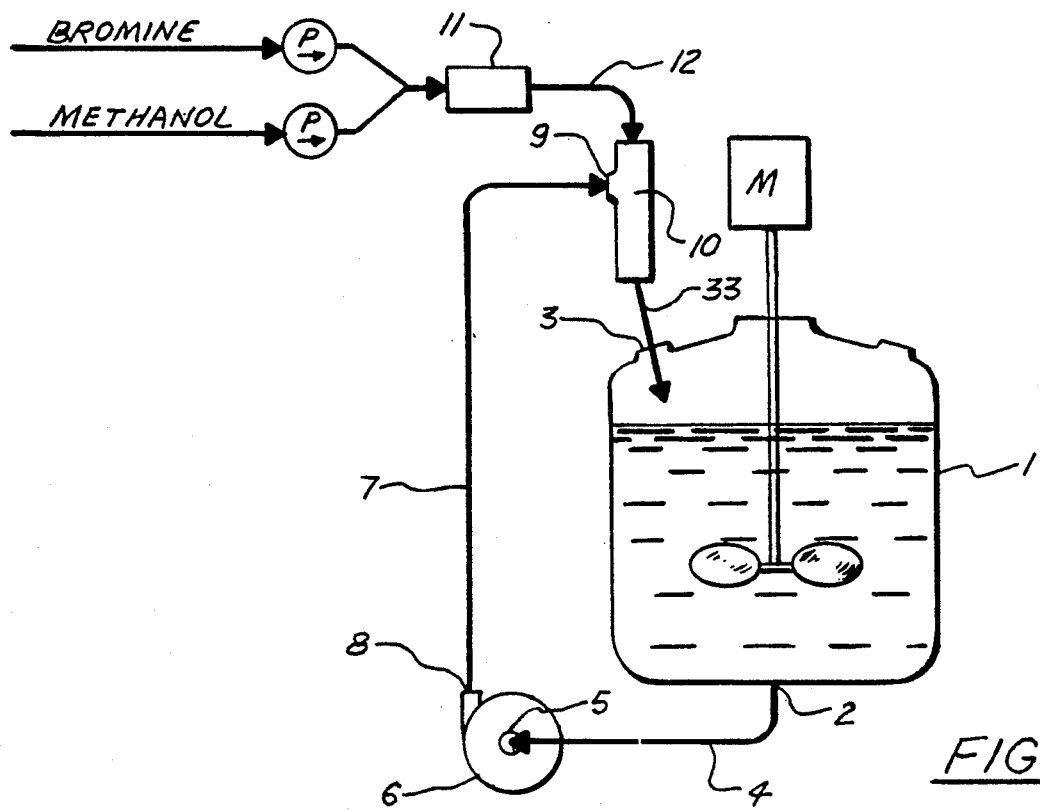
FIG. 1 is a schematic representation of an embodiment of the process showing the reaction vessel and the external closed loop flow path through an impingement mixer.
Figure 2:
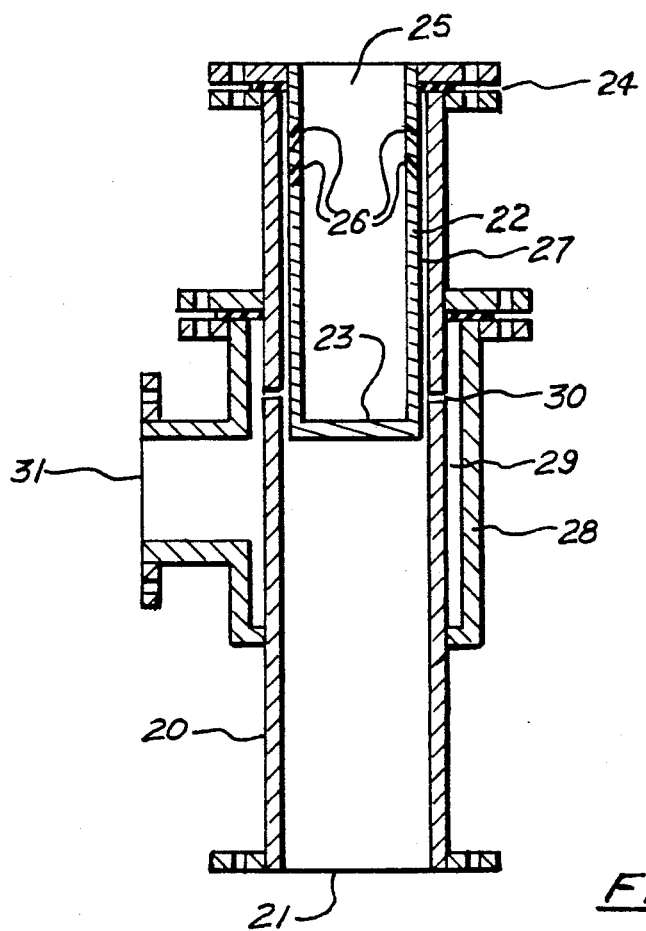
FIG. 2 is a cross-section not to scale of a suitable impingement mixer in which pre-mixed bromine-methanol feed is impinged with a circulating reaction mixture in an annular space.

This invention relates to a process for producing a tetrabromobisphenol-A (TBBPA) predominant product in high yield and high purity, the process comprising: (a) feeding a first stream comprising bromine dissolved in methanol to an impingement mixer; (b) impinging a second stream with the first stream in the impingement mixer to rapidly mix the streams and to form a reaction mixture thereof, the second stream, at process initiation, comprising bisphenol-A dissolved in methanol and, after at least one cycle of the process, comprising brominated bisphenol-A; (c) conducting the reaction mixture to a reaction vessel which holds reactor contents which, at process initiation, comprise bisphenol-A dissolved in methanol and, after at least one cycle of the process comprise brominated bisphenol-A; )d) removing a portion of the reactor contents from the reaction vessel to form the second stream; (e) continuing steps (a), (b), (c), and (d) until the amount of bromine fed is about 4 moles of bromine per mole of bisphenol-A used in the process and the weight ratio of TBBPA to methanol is about 0.67–0.68 when the bromination reaction is substantially complete; and (f) subsequent to (e), adding an amount of water to the reaction vessel which holds the reactor contents so as to obtain an increase in recovery of the product predominant in tetrabromobisphenol-A.

The improvement of the present process enables the production of TBBPA on a large scale at high yield and a product that is substantially lower in organic impurities and in HBr impurities while achieving an increase in recovery of product of about 5% or more based on the theoretical amount of TBBPA which may be produced.

A key feature of the process of this invention is the weight ratio of TBBPA predominant product to methanol in the reaction vessel when the bromination reaction is substantially complete. A significantly improved product (e.g. a product with both a low level of organic impurity and a low level of HBr impurity) can be obtained when the weight ratio of TBBPA to methanol is about 0.6–0.72. A more preferred weight ratio of TBBPA to methanol is about 0.65–0.70 with the most preferable ratio being about 0.67–0.68 parts TBBPA per each part of methanol.

The bromination reaction is substantially complete when essentially all of the bisphenol-A used as a reactant has about 4 bromine atoms per molecule.

The amount of methanol in the reaction vessel when the bromination reaction is substantially complete can be adjusted in several ways. Methanol is used to dissolve the bisphenol-A as well as provide solvent for the bromine feed to the impingement mixer. The amount of methanol used to dissolve the bisphenol-A and the amount of methanol used to provide a solvent for the bromine feed solution can be adjusted within wide limits as long as the preferable ratio of TBBPA product to methanol is obtained when the bromination reaction is substantially complete.

During the course of the bromination reaction HBr is formed which in turn reacts with methanol at the process conditions to form methyl bromide. The amount of methanol which reacts to form methyl bromide may be affected by adjusting the process conditions (e.g. cook time and/or temperature).

During the bromination reaction, methanol is vaporized and a portion of the methanol is refluxed to the reaction vessel. Another portion of methanol is collected as condensate and utilized as a solvent for bisphenol-A is a subsequent batch. The amount of methanol removed as condensate can be easily adjusted to yield the desired ratio of TBBPA product to methanol. Other means for achieving the preferred TBBPA product to methanol ratio are within the scope of this invention.

At process initiation, vessel 1, preferably a glass or glass-lined vessel, is charged with methanol and bisphenol-A. The amount of methanol used to dissolve the bisphenol-A can vary over a wide range and this amount of methanol contributes to the amount of methanol in the reaction vessel when the bromination reaction is substantially complete. A useful range is about 1.0–6 parts by weight methanol per each part bisphenol-A. A more preferred range is about 2–4 parts by weight methanol per each part bisphenol-A and the most preferred amount is about 3.0:1.

The process is then started by activating pump 6 which withdraws reaction mixture (initially methanol-bisphenol-A solution) from bottom outlet 2 through outlet conduit 4. Pump 6 is preferably of the centrifugal type and receives the reaction mixture at suction intake 5. The reaction mixture is pumped through discharge port 8 and riser conduit 7 to impingement mixer 10 which will be described in detail later.

Concurrently bromine and methanol are pumped at a controlled rate from the storage through conventional static mixer 11.

The bromine/alcohol ratio can vary widely. The more dilute the bromine solution, the better the results. However, excessive dilution causes an unacceptable drop in production per unit volume of reactor. A useful range in which to operate is about 1–4 parts by weight bromine per each part methanol. A more preferred range is about 1–3 parts bromine per each part methanol. The most preferred amount is about 2 parts bromine per each part methanol. The methanol used with the bromine feed also contributes significantly to the amount of methanol in the reaction vessel when the bromination is substantially complete. This ratio, therefore, has an impact on the purity of the TBBPA product thus obtained.

The ratio of (1) the volume of the reaction mixture recirculation through the external loop and impingement mixer to (2) the volume of the methanol-bromine solution feed can vary over a wide range. Preferably the volume of the reaction mixture recirculation will exceed the volume of the methanol-bromine feed. A useful range is about 0.80–30:1. A more useful range is about 15-18:1.

The amount of methanol-bromine solution should be an amount that supplies sufficient bromine to make an acceptable product. The stoichiometric requirement is 4 moles of bromine per mole of bisphenol-A. A useful range in which to operate is about 3.9–4.1 moles of bromine per mole of bisphenol-A and the most preferred range is 3.95–4.05 moles bromine per mole of bisphenol-A.

From static mixer 11 the bromine-methanol solution passes through conduit 12 to impingement mixer 10.

Impingement mixer 10 comprises an outer substantially cylindrical shell 20 open at its discharge end 21. Hollow distribution member 22, essentially closed at one end 23, is axially located inside shell 20 and sealably engaged with shell 20 at end 24 opposite discharge end 21. Distribution member 22 has an inlet 25 and a plurality of orifices 26 circumferentially located in the sidewall of member 22 forming a plurality of passages from the hollow interior of member 22 into annular space 27 between member 22 and shell 20.

Outer axial cylindrical member 28 is sealably engaged at both ends to shell 20 forming outer annular chamber 29. A circumferential slit 30 extends around shell 20 forming a narrow circumferential passage from annular chamber 29 into annular space 27. Side outlet 31 in member 28 is adapted to connect to riser conduit 7 to receive the reaction mixture.

The bromine-methanol solution from static mixer 11 passes through conduit 12 to inlet 25 of distribution member 22. The bromine-methanol solution is forced at high velocity through orifice 26 into annular space 27. Meanwhile reaction mixture from riser conduit 7 enters annular chamber 29 through side inlet 31 and is forced at high velocity through slit 30 into annular space 27.

The bromine-methanol solution and the reaction mixture impinge in annular space 27 and the resultant mixture passes through discharge end 21 which is operably connected to feed conduit 33 which feeds the mixture back into reactor 1.

Rapid mixing of the bromine-methanol and bisphenol-A-methanol is highly preferred in order to obtain the best results with the process of this invention. The present process is a facile way of providing the high agitation so as to achieve the rapid mixing mentioned in our prior patent U.S. Pat. No. 4,628,124 issued Dec. 9, 1986.

The bromine-methanol solution may be fed to the circulating reaction mixture at an initial temperature that is ambient or lower although this is not essential. For example the bromine-methanol feed can be started while the reactor contents and circulating reaction mixture is at temperatures from $-10°$ C. up to about 30° C. or somewhat higher if that is what the liquid temperature happens to be. As the feed progresses the temperature will rise due to the heat of the reaction. Sometime during the feed, the reactor temperature will attain reflux conditions and the reflux can be continued through the end of the feed of the bromine-methanol solution although reflux is not essential as long as the reaction is continued long enough to substantially complete the bromination of essentially all of the bisphenol-A reactant. After this, heat can be applied to maintain reflux for a short period of time of say 10 minutes to 1 hour to assure completion of the reaction.

During the bromine-methanol feed, the bromination of bisphenol-A forms HBr some of which reacts with methanol to form methyl bromide. The methyl bromide vaporizes and can be collected from the off-gas and marketed as a commercial product for its many known uses such as soil fumigation.

The bromination reaction is conducted at a temperature in the range of from about 15° C. to about reflux. Preferably the temperature is in a range of from about 20° C. to about reflux and most preferably the temperature of reaction ranges from about 35° C. to about reflux.

Pressure is not critical to the process of this invention as the bromination reaction can be carried at pressures ranging from subatmospheric to superatmospheric. It is desirable to operate with a pressure of about 10–15 psig in order to minimize the vaporization of reactants from the reaction vessel.

Subsequent to obtaining the TBBPA predominant product, the product is recovered by adding an amount of water to the reaction vessel containing the mixture comprising the TBBPA product, methanol, excess bromine, methylene bromide, and HBr. It has been found that the amount of water added relative to the amount of TBBPA product in the reaction mixture has an effect on the amount of product thus recovered. A useful amount of water to add is in the range of from about 0.1 to about 5 parts of water per part of TBBPA product. A preferred amount of water is in the range of from about 0.2 to about 2.0 with the most preferred amount in the range of from about 0.6 to about 0.8 parts of water per part of TBBPA product.

TBBPA can be recovered from the mixture using conventional methods such as filtration, decantation, settling, centrifugation and the like. For example, after the water addition, the final mixture can be filtered and the TBBPA product recovered as a wet cake. The wet cake can then be dried in an oven to remove water, methanol, bromine, HBr and other volatiles.

The following example is given by way of comparison.

EXAMPLE 1

Comparative Example

In a glass lined reaction vessel was placed methanol and bisphenol-A with a weight ratio of 1.80 parts of methanol per part of bisphenol-A. When the bisphenol-A was dissolved, the solution was circulated through an external loop which included an impingement mixer at the rate of 250 gallons per minute. A bromine-methanol solution (2:1 bromine:methanol weight ratio) was pumped to the impingement mixer at a rate of about 300 lbs/min. The bromine solution feed was continued until 1% stoichiometric excess over that required for TBBPA had been fed. The temperature in the reaction vessel during bromine-methanol feed rose from 22° C. to reflux over 20 minutes. Reflux was maintained until the bromine-methanol feed was complete. Following feed completion, the recirculation reaction mixture was stopped and reflux was continued for 30 minutes. During the bromination, about 0.46 parts of methanol per part bisphenol-A was vaporized from the reaction vessel and recovered as distillate and about 0.08 parts of methanol per part of bisphenol-A reacted to form methyl bromide. At the end of the reflux period a ratio of about 1:1.08 parts of water per part of bisphenol-A reactant was added to the reaction vessel. Based on theoretical production amounts, about 88% of the product was recovered. The product was analyzed after drying and the HBr impurity in the TBBPA product ranged from about 90 to about 125 ppm HBr with an average of about 105 ppm HBr in the product.

Example 2

Following the general procedure of Example 1, additional batches of TBBPA product were made except that in these batches, the weight ratio of methanol to bisphenol-A initially in the reaction vessel was 3.0 parts methanol per part of bisphenol-A and the ratios of TBBPA product to methanol when the reaction was substantially complete was about 0.67 parts of TBBPA per part of methanol. The product was then collected and analyzed. In these batches, the amount of HBr impurity ranged from about 37 to about 87 ppm HBr with an average of about 56 ppm HBr in the product.

In the following examples, the amount of water added to the reaction vessel after the reflux period was varied. The ratio of methanol to TBBPA product remained the same as in Example 2. As an indication of the amount of TBBPA product recovered the weight percent of TBBPA in the centrate was analyzed. The lower the amount of TBBPA product in the centrate, the greater the recovery of TBBPA product from the batch.

Example 3

In this example, the weight ratio of water to bisphenol-A was about 1.17:1 parts of water per part of bisphenol-A. The results are given in Table I.

TABLE I

| Run | Wt % TBBPA in Centrate | HBr Impurities (ppm) |
|---|---|---|
| 1 | 2.1 | 51 |
| 2 | 1.7 | 48 |
| 3 | 1.5 | 54 |
| 4 | 1.2 | 47 |
| 5 | 1.8 | 53 |

EXAMPLE 4

The weight ratio of water to bisphenol-A reactant in this example was about 1.33:1 parts of water per part of bisphenol-A. Results are given in Table II.

TABLE II

| Run | Wt % TBBPA in Centrate | HBr Impurities (ppm) |
|---|---|---|
| 1 | 1.40 | 52 |
| 2 | 1.30 | 50 |
| 3 | 0.85 | 69 |
| 4 | 0.85 | 85 |
| 5 | 0.60 | 60 |

EXAMPLE 5

For the runs shown in Table III, the weight ratio of water to bisphenol-A was about 1.5:1 parts of water per part of bisphenol-A.

TABLE III

| Run | Wt % TBBPA in Centrate | HBr Impurities (ppm) |
|---|---|---|
| 1 | 1.40 | 70 |
| 2 | 0.65 | 83 |
| 3 | 1.70 | 66 |
| 4 | 0.70 | 62 |
| 5 | 0.48 | 54 |

EXAMPLE 6

For the runs shown in Table IV, the weight ratio of water to bisphenol-A was about 1.67:1 and the amount of product recovered was about 95.6% of theoretical.

TABLE IV

| Run | Wt % TBBPA in Centrate | HBr Impurities (ppm) |
|---|---|---|
| 1 | 0.50 | 60 |
| 2 | 0.60 | 60 |
| 3 | 0.60 | 52 |
| 4 | 0.70 | 51 |
| 5 | 0.40 | 59 |
| 6 | 0.50 | 65 |
| 7 | 0.45 | 53 |

The results show that the improved process achieves a very high purity TBBPA and an increased recovery of the TBBPA product on a commercial scale.

The improved process is applicable to the bromination of other bisphenols. These are compounds of the structure:

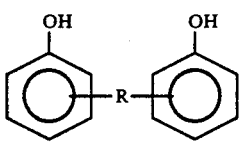

wherein R is a divalent aliphatic hydrocarbon group of 1-4 carbon atoms or a direct bond between the two benzene rings. Representative examples are 4,4'-methylenebisphenol, 2,2'-methylenebisphenol, 2,4'-methylenebisphenol, 4,4'-ethylidenebisphenol, 2,2'-ethylidenebisphenol, 2,4'-ethylidenebisphenol, 2,2'-isopropylidenebisphenol, 2,4'-isopropylidenebisphenol, 4,4'-butylidenebisphenol, 2,2'-butylidenebisphenol, 4,4'-bisphenol, 2,2'-bisphenol, 2,4'-bisphenol and the like. These bisphenols can be substituted for the bisphenol-A, i.e., 4,4'-isopropylidenebisphenol, used in the foregoing description and examples of the present invention. All of the products can be used as fire retardants in a broad range of organic materials normally susceptible to combustion in the presence of air and an ignition source.

Other variations are possible within the spirit and scope of the appended claims.

What is claimed is:

1. A process for producing a tetrabromobisphenol-A predominant product in a high yield and high purity, said process comprising:
   (a) feeding a first stream comprising bromine dissolved in methanol to an impingement mixer;
   (b) impinging a second stream with said first stream in said impingement mixer to rapidly mix said streams and to form a reaction mixture thereof, said second stream, at process initiation, comprising bisphenol-A dissolved in methanol and, after at least one cycle of said process, comprising brominated bisphenol-A;
   (c) conducting said reaction mixture to a reaction vessel which holds reactor contents which, at process initiation, comprise bisphenol-A dissolved in methanol and, after at least one cycle of said process comprise brominated bisphenol-A;
   (d) removing a portion of said reactor contents from said reaction vessel to form said second stream;
   (e) continuing steps (a), (b), (c), and (d) until the amount of bromine fed is about 4 moles of bromine per mole of bisphenol-A used in said process and the weight ratio of TBBPA to methanol is about 0.67-0.68 when the bromination reaction is substantially complete; and
   (f) subsequent to (e), adding an amount of water to said reaction vessel which holds said reactor contents so as to obtain an increase in recovery of said product predominant in tetrabromobisphenol-A.

2. The process of claim 1 wherein the weight ratio of said bromine to said methanol in said first stream is about 2:1.

3. The process of claim 1 wherein the volume ratio of said second stream to said first stream is within the range of about 0.8-30:1.

4. The process of claim 2 wherein the volume ratio of said second stream to said first stream is within the range of about 0.8-30:1.

5. The process of claim 1 wherein the volume ratio of said second stream to said first stream is within the range of about 10-20:1.

6. The process of claim 2 wherein the temperature in said reaction vessel attains reflux conditions during the course of the reaction.

7. The process of claim 1 wherein said amount of water added to said reaction vessel in step (f) is about 0.6-0.8 parts of water per part of tetrabromobisphenol-A product.

8. The process of claim 1 wherein said process is conducted at a temperature in the range of from about 35° C. to about reflux.

9. In a process for producing a product predominant in tetrabromobisphenol-A in high yield and high purity using an impingement mixer to rapidly mix a first stream comprising bromine dissolved in methanol and a second stream, at process initiation, comprising bisphenol-A dissolved in methanol and, after at least one cycle of said process, said second stream comprising brominated bisphenol-A, said first and second streams being conducted to a reaction vessel which holds reactor contents a portion of which reactor contents is removed to form said second stream; the improvement comprising:
   (a) adjusting the weight ratio of TBBPA to methanol such that the ratio is about 0.67-0.68 when the bromination reaction is substantially complete; and
   (b) subsequent to (a), adding an amount of water to said reaction vessel which holds said reactor contents so as to obtain an increase in recovery of said product predominant in tetrabromobisphenol-A.

10. The process of claim 9 wherein the weight ratio of said bromine to said methanol in said first stream is about 2:1.

11. The process of claim 9 wherein the volume ratio of said second stream to said first stream is within the range of about 0.8-30:1.

12. The process of claim 10 wherein the volume ratio of said second stream to said first stream is within the range of about 0.8-30:1.

13. The process of claim 9 wherein the volume ratio of said second stream to said first stream is within the range of about 10-20:1.

14. The process of claim 10 wherein the temperature in said reaction vessel attains reflux conditions during the course of the reaction.

15. The process of claim 9 wherein said amount of water added to said reaction vessel in step (f) is about 0.6-0.8 parts of water per part of tetrabromobisphenol-A product.

16. The process of claim 9 wherein said process is conducted at a temperature in the range of from about 35° C. to about reflux.

* * * * *